US012629158B2

(12) United States Patent (10) Patent No.: US 12,629,158 B2
Tsusaka (45) Date of Patent: May 19, 2026

(54) CAM MODULE, FEMORAL TRIAL, INTERCONDYLAR CUTTING GUIDE, AND SYSTEM

(71) Applicant: KYOCERA Corporation, Kyoto (JP)

(72) Inventor: Shinya Tsusaka, Ibaraki (JP)

(73) Assignee: KYOCERA Corporation, Kyoto (JP)

( * ) Notice: Subject to any disclaimer, the term of this patent is extended or adjusted under 35 U.S.C. 154(b) by 461 days.

(21) Appl. No.: 18/019,314

(22) PCT Filed: Aug. 2, 2021

(86) PCT No.: PCT/JP2021/028548
§ 371 (c)(1),
(2) Date: Feb. 2, 2023

(87) PCT Pub. No.: WO2022/030427
PCT Pub. Date: Feb. 10, 2022

(65) Prior Publication Data
US 2023/0277198 A1 Sep. 7, 2023

(30) Foreign Application Priority Data

Aug. 4, 2020 (JP) ................................. 2020-132568

(51) Int. Cl.
*A61F 2/38* (2006.01)
*A61B 17/17* (2006.01)
*A61F 2/46* (2006.01)

(52) U.S. Cl.
CPC ........ *A61B 17/1764* (2013.01); *A61F 2/3859* (2013.01); *A61F 2/4684* (2013.01)

(58) Field of Classification Search
CPC ........................................................ A61F 2/38
See application file for complete search history.

(56) References Cited

U.S. PATENT DOCUMENTS

| | | | | |
|---|---|---|---|---|
| 5,100,409 A | * | 3/1992 | Coates | ............... A61B 17/1764 |
| | | | | 606/88 |
| 2011/0307067 A1* | | 12/2011 | Dees | ..................... A61F 2/3859 |
| | | | | 623/20.35 |
| 2012/0323334 A1* | | 12/2012 | Jones | ................... A61B 17/155 |
| | | | | 623/20.14 |
| 2013/0204265 A1 | | 8/2013 | Capek et al. | |
| 2015/0366671 A1 | | 12/2015 | Dees | |
| 2017/0333210 A1 | | 11/2017 | Lashure et al. | |
| 2017/0333211 A1* | | 11/2017 | Flakne | .................. A61F 2/3886 |

(Continued)

FOREIGN PATENT DOCUMENTS

| | | |
|---|---|---|
| JP | 2010-508063 A | 3/2010 |
| JP | 3165932 U | 2/2011 |

(Continued)

*Primary Examiner* — David W Bates
(74) *Attorney, Agent, or Firm* — Procopio, Cory, Hargreaves & Savitch LLP

(57) ABSTRACT

To stably maintain a fitting state to an opening portion by reducing a likelihood of displacement and detachment from the opening portion of a femoral trial. A cam module of the present disclosure includes a first connection portion disposed at a first end portion provided in a side wall portion and connectable to the femoral trial, and a second connection portion disposed at a second end portion provided in the side wall portion and connectable to the femoral trial.

7 Claims, 15 Drawing Sheets

(56)              References Cited

U.S. PATENT DOCUMENTS

2018/0296353 A1    10/2018  Dees
2019/0029847 A1 *   1/2019  Nguyen  ............... A61B 17/155
2025/0000661 A1 *   1/2025  Aram  .................... A61F 2/3886

FOREIGN PATENT DOCUMENTS

JP            5379009  B2    12/2013
JP         2014-522671  A     9/2014
JP         2019-516489  A     6/2019

* cited by examiner

CAM MODULE, FEMORAL TRIAL, INTERCONDYLAR CUTTING GUIDE, AND SYSTEM

TECHNICAL FIELD

The present disclosure relates to a cam module, a femoral trial, an intercondylar cutting guide, and a system for use in knee joint replacement surgery.

BACKGROUND OF INVENTION

In general, in surgery for replacing a knee joint having a reduced function with an artificial knee joint, before the artificial knee joint is installed in a bone, a femoral trial for trial fitting having substantially the same shape as that of the artificial knee joint is installed in the bone, whereby trial reduction is performed. An example of replacement surgery for the artificial knee joint using the femoral trial is disclosed in Patent Document 1. In a femoral trial component (femoral trial) disclosed in Patent Document 1, an opening portion for removing bone in a box shape is formed. By fitting a cam module into the opening portion, the shape becomes substantially the same as that of the artificial knee joint, thereby enabling trial reduction to be performed.

CITATION LIST

Patent Literature

Patent Document 1: JP 5379009 (registered on Oct. 4, 2013)

SUMMARY

A cam module according to the present disclosure includes: a pair of side wall portions, each side wall portion including a first end portion and a second end portion different from the first end portion in a longitudinal direction; a first connection portion disposed at the first end portion of the pair of side wall portions and connectable to a femoral trial; and a second connection portion disposed at the second end portion of the pair of side wall portions and connectable to the femoral trial, in which the cam module fits into an opening portion of the femoral trial.

A femoral trial according to the present disclosure includes: an opening portion for fitting a cam module including a pair of side wall portions, each side wall portion including a first end portion and a second end portion different from the first end portion in a longitudinal direction, a first connection portion disposed at the first end portion of the pair of side wall portions, and a second connection portion disposed at the second end portion of the pair of side wall portions, wherein the opening portion includes: a support portion supporting the first connection portion disposed in the cam module on an front side; and a contact portion on a rear side of which the second connection portion disposed in the cam module comes into contact.

An intercondylar cutting guide according to the present disclosure includes: a cutting guide portion exposed in accordance with a shape of an opening portion of a femoral trial; an attachment portion configured to attach the cutting guide portion to a predetermined position on the femoral trial by a magnetic force, in which the intercondylar cutting guide guides an osteotomy through the opening portion.

A femoral trial according to the present disclosure includes: an attachment surface to be attached to a bone of a knee joint; a joint-side surface opposite to the attachment surface; an opening portion disposed to pass through the attachment surface and the joint-side surface and configured to be fitted with a cam module; and a trial-side attachment portion to which an intercondylar cutting guide comprising an attachment portion attached to a predetermined position by a magnetic force can be attached in order to guide cutting of a bone from the opening portion, in which the trial-side attachment portion is made of a material to which the intercondylar cutting guide can be attached by a magnet provided in the intercondylar cutting guide in a state in which the intercondylar cutting guide is set at the predetermined position.

DESCRIPTION OF EMBODIMENTS

First Embodiment

In Patent Document 1, a rotation pile portion is provided at one end portion of a cam module, and the cam module is fitted into an opening portion of a femoral trial component with the rotation pile portion as a rotation center. The cam module is held at a predetermined position in the opening portion of a femoral trial component by a holding portion provided in the cam module.

However, since the holding portion of the cam module is provided in the vicinity of the center in the longitudinal direction, stable support of the cam module is difficult.

Therefore, the cam module is likely to deviate and detach from the opening portion of the femoral trial component, and stably maintaining the fitting state to the opening portion is difficult.

An aspect of the present disclosure provides a cam module that is less likely to be displaced and detached from an opening portion of a femoral trial and can stably maintain a fitting state to the opening portion.

An embodiment of the present disclosure will be described in detail below. The cam module described in the present embodiment is a cam module to be fitted into the opening portion of the femoral trial used at the time of knee joint replacement surgery.

Femoral Trial

Figure 1:
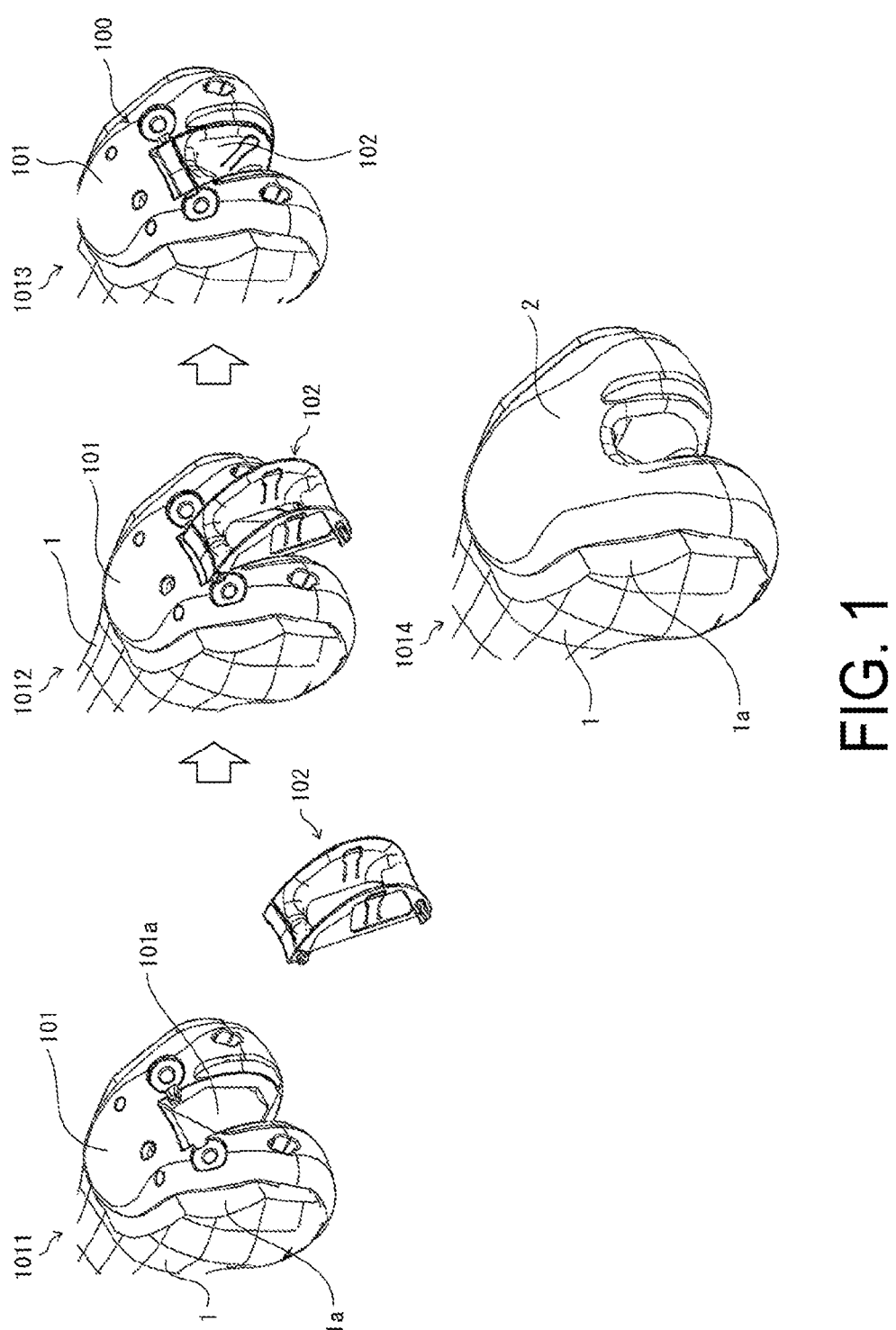
FIG. 1 is a diagram illustrating a procedure for replacing a knee joint with an artificial knee joint using a femoral trial according to a first embodiment of the present disclosure.

FIG. 1 is a view for explaining a procedure for replacing a knee joint using a femoral trial 100 with an artificial knee joint 2.

As illustrated in FIG. 1, the femoral trial 100 includes a trial body 101 installed in a bone 1, and a cam module 102 attached to the trial body 101. The part of the femoral trial 100 close to the femur is referred to as the bone side, and the opposite side is referred to as the articular surface side. By attaching the cam module 102 to the trial body 101, the femoral trial 100 has a substantially identical or similar shape to the shape of the artificial knee joint 2 in trial reduction. The trial body 101 and the cam module 102 are formed of an arbitrary metal material such as a zirconium alloy, a cobalt-chromium alloy, stainless steel, or titanium.

As indicated by reference sign 1011 in FIG. 1, the trial body 101 is attached after a knee joint 1a of the bone 1 is processed into a predetermined shape. The shape of the knee joint 1a of the bone 1 is cut into a shape corresponding to the attachment surface of the artificial knee joint 2. If the attachment surface of the artificial knee joint 2 is, for example, substantially pentagonal in a sagittal section, the knee joint 1a of the bone 1 is processed to have five surfaces in accordance with the attachment surface of the artificial knee joint 2 (for example, FIG. 8).

In the trial body 101, an opening portion 101a is formed at a position corresponding to a portion where an osteotomy of the knee joint 1a needs to be further performed in a state in which the trial body 101 is attached to the bone 1. In the present disclosure, the knee joint 1a is a distal intercondylar portion of the femoral bone, i.e., the portion between the medial and lateral condyles. The osteotomy of the knee joint 1a is performed prior to proper attachment of the cam module 102.

After the osteotomy of the knee joint 1a of the bone 1 is performed through the opening portion 101a of the trial body 101, the cam module 102 is attached to the opening portion 101a as indicated by reference signs 1012 and 1013 in FIG. 1. In this manner, the femoral trial 100 is completed by attaching the cam module 102 to the trial body 101. As indicated by reference sign 1014 in FIG. 1, the femoral trial 100 has a substantially identical or similar shape to the shape of the artificial knee joint 2 as a final product. Therefore, the femoral trial 100 can perform the trial function of the artificial knee joint 2. Details of a method of attaching the cam module 102 will be described below.

Outline of Cam Module

Figure 2:
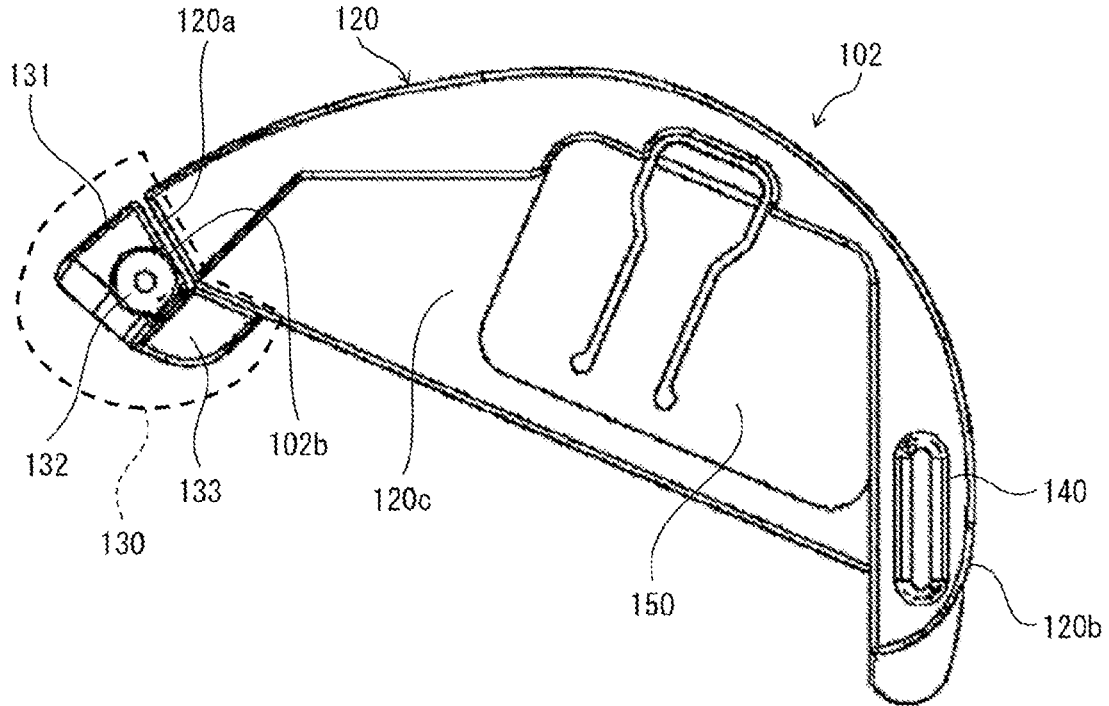
FIG. 2 is a side view of a cam module attached to the femoral trial illustrated in FIG. 1.
Figure 3:
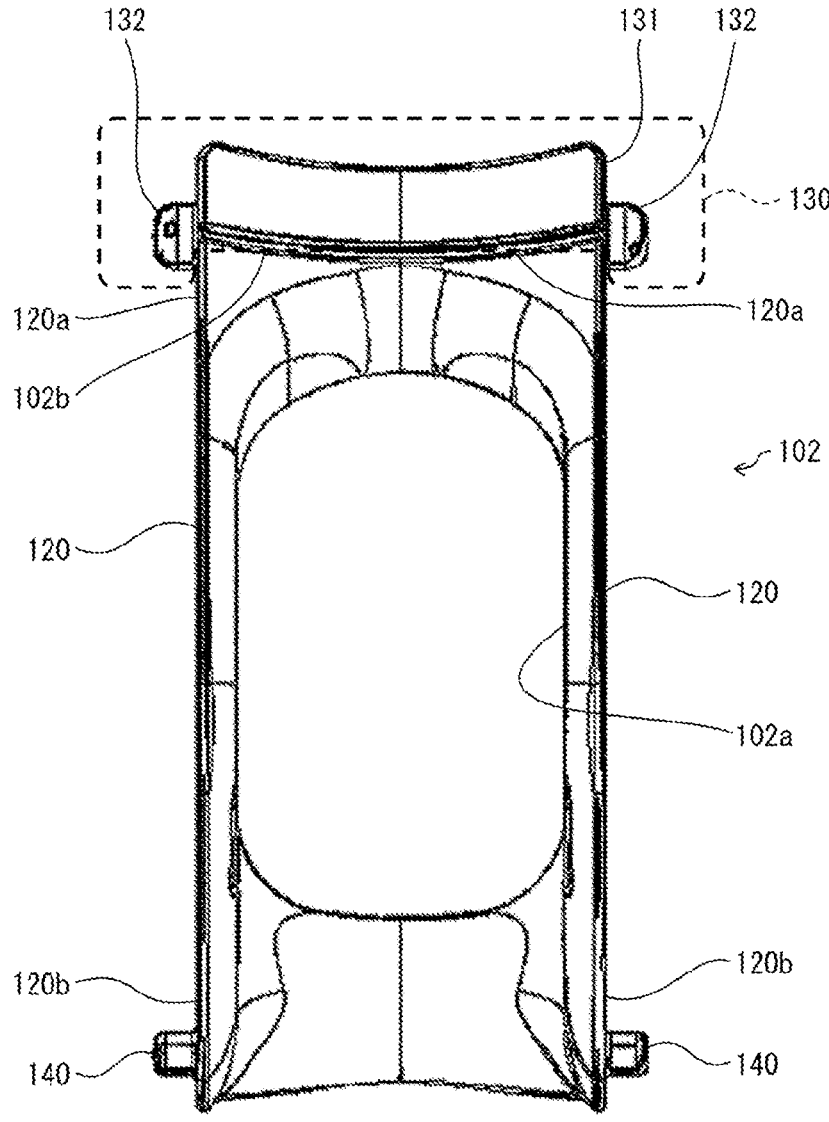
FIG. 3 is a rear view of the cam module attached to the femoral trial illustrated in FIG. 1.

FIG. 2 is a side view of the cam module 102. FIG. 3 is a rear view of the cam module 102.

As illustrated in FIG. 3, the cam module 102 has a pair of side wall portions 120 which are disposed to face each other to form an opening portion 102a at the center of the cam module 102. As illustrated in FIG. 2, each of the side wall portions 120 has a first end portion 120a and a second end portion 120a different from the first end portion 120b in the longitudinal direction.

The first end portion 120a is provided with a first connection portion 130 for connecting to the femoral trial 100. A slit 102b having a predetermined depth is formed in a connection portion between the first end portion 120a and the first connection portion 130.

The second end portion 120b is provided with a second connection portion 140 for connecting to the femoral trial 100.

The first connection portion 130 includes a body portion 131 connected to the first end portion 120a of the side wall portion 120, and a rotation pile portion 132 and a base portion 133 provided in the body portion 131.

The rotation pile portion 132 is formed to protrude outward in a lateral direction of the side wall portion 120, and functions as a rotation shaft upon the cam module 102 being fitted into the opening portion 101a of the trial body 101 constituting the femoral trial 100.

The base portion 133 is used to determine whether or not the osteotomy is normally performed. To be specific, the base portion 133 has a shape such that the base portion 133 protrudes toward the bone, and is long enough not to come into contact with the bone 1 upon the cam module 102 being rotated to a predetermined position on the opening portion 101a of the trial body 101 while the osteotomy is normally performed. A detailed description for determining whether or not the osteotomy is normally performed by the base portion 133 will be described below.

The second connection portion 140 is formed to protrude outward in the lateral direction of the side wall portion 120, and functions as a stopper upon the cam module 102 being fitted into the opening portion 101a of the trial body 101 constituting the femoral trial 100.

In the second connection portion 140, the cam module 102 rotates to a predetermined position in the opening portion 101a in a state in which the rotation pile portion 132 of the first connection portion 130 is rotatably supported at a predetermined position in the opening portion 101a of the trial body 101. Upon the cam module 102 being rotated to a predetermined position in the opening portion 101a, the second connection portion 140 is accommodated in an accommodation portion 101c (see reference sign 1082 in FIG. 8) formed at a predetermined position on the trial body 101 of the femoral trial 100. Thus, the cam module 102, which is rotating about the rotation pile portion 132, can be stopped at a predetermined position on the opening portion 102a of the trial body 101.

An urging member 150 is provided on each side surface 120c of the pair of side wall portions 120. The urging member 150 exerts an urging force toward the trial body 101 upon the cam module 102 being fitted to a predetermined position in the opening portion 101a of the trial body 101. Accordingly, upon the cam module 102 being fitted to a predetermined position on the opening portion 101a of the trial body 101, the urging force of the urging member 150 acts to make the cam module 102 less likely to be detached.

Attachment of Cam Module

The attachment of the cam module 102 to the trial body 101 illustrated in FIGS. 2 and 3 will be described based on the structural features of the cam module 102.

Rotation Pile Portion 132

Figure 4:
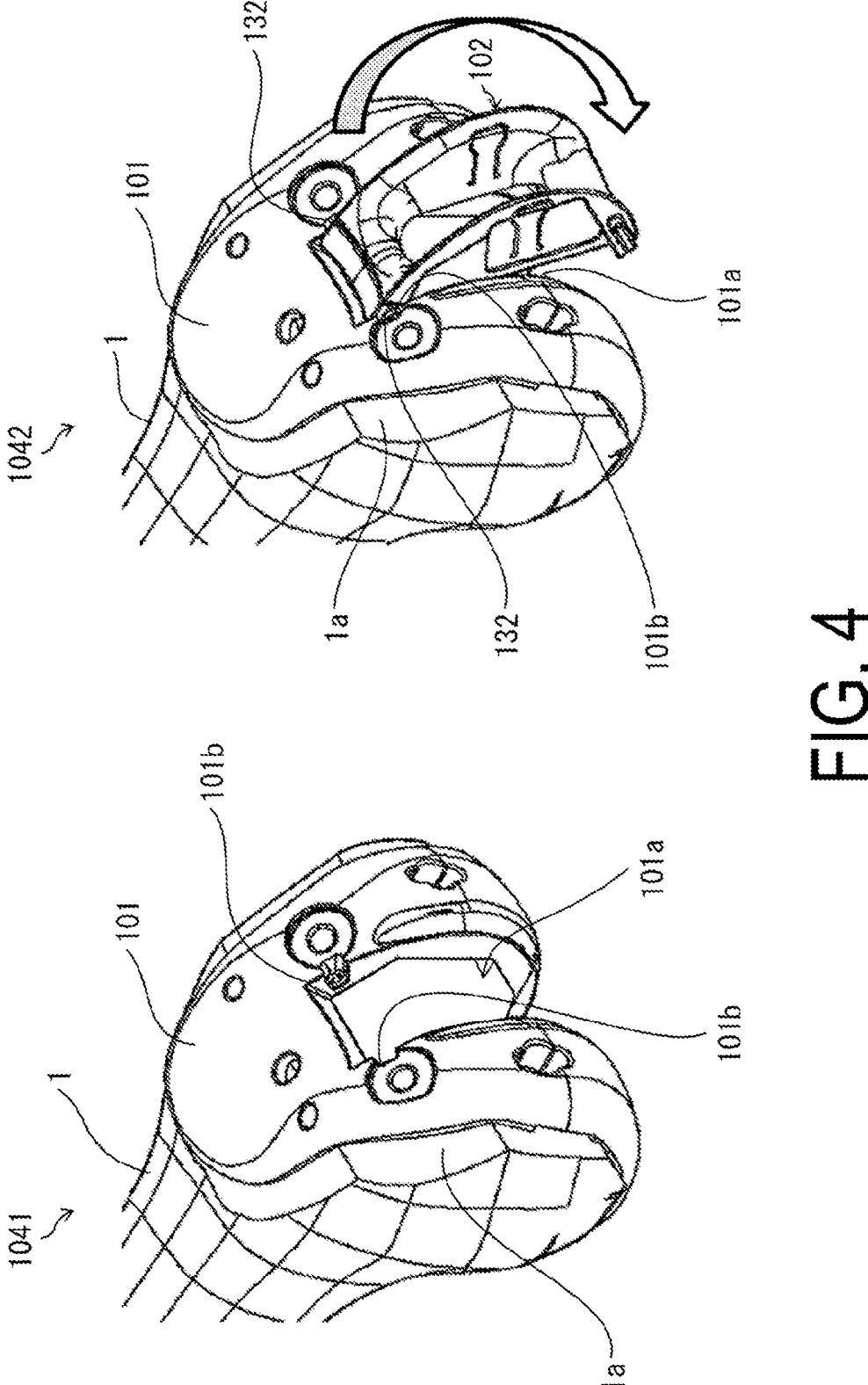
FIG. 4 is a view for explaining a method of attaching the cam module illustrated in FIG. 1 to the femoral trial.

As indicated by reference sign 1041 in FIG. 4, the rotation pile portion 132 of the cam module 102 is inserted, as indicated by reference sign 1042 in FIG. 4, into each groove portion 101b formed on both sides of the upper portion of the opening portion 101*a* of the trial body 101 attached to a predetermined position on the bone 1.

The cam module 102 is rotated in the direction of the arrow (toward the opening portion 101*a*) with the rotation pile portion 132 as a rotation axis, and the cam module 102 is attached to a predetermined position on the opening portion 101*a* of the trial body 101.

In this manner, the cam module 102 can be easily attached to the opening portion 101*a* of the trial body 101 by merely inserting the rotation pile portion 132 into the groove portion 101*b* of the trial body 101.

That is, the cam module 102 rotates to a predetermined position on the opening portion 101*a* of the trial body 101 about the rotation pile portion 132 of the first connection portion 130. As a result, the second connection portion 140 formed at the other end portion of the side wall portion 120 in the longitudinal direction comes into contact with the femoral trial 100, and the rotation of the cam module 102 is stopped. At this time, the urging member 150 may also come into contact with the femoral trial 100. This makes it easier to fit the cam module 102 because only the rotation pile portion 132 needs to be positioned, compared with fitting the cam module 102 by positioning all of the first connection portion 130, the second connection portion 140, and the urging member 150 at the same time.

Slit 102*b*

Figure 5:
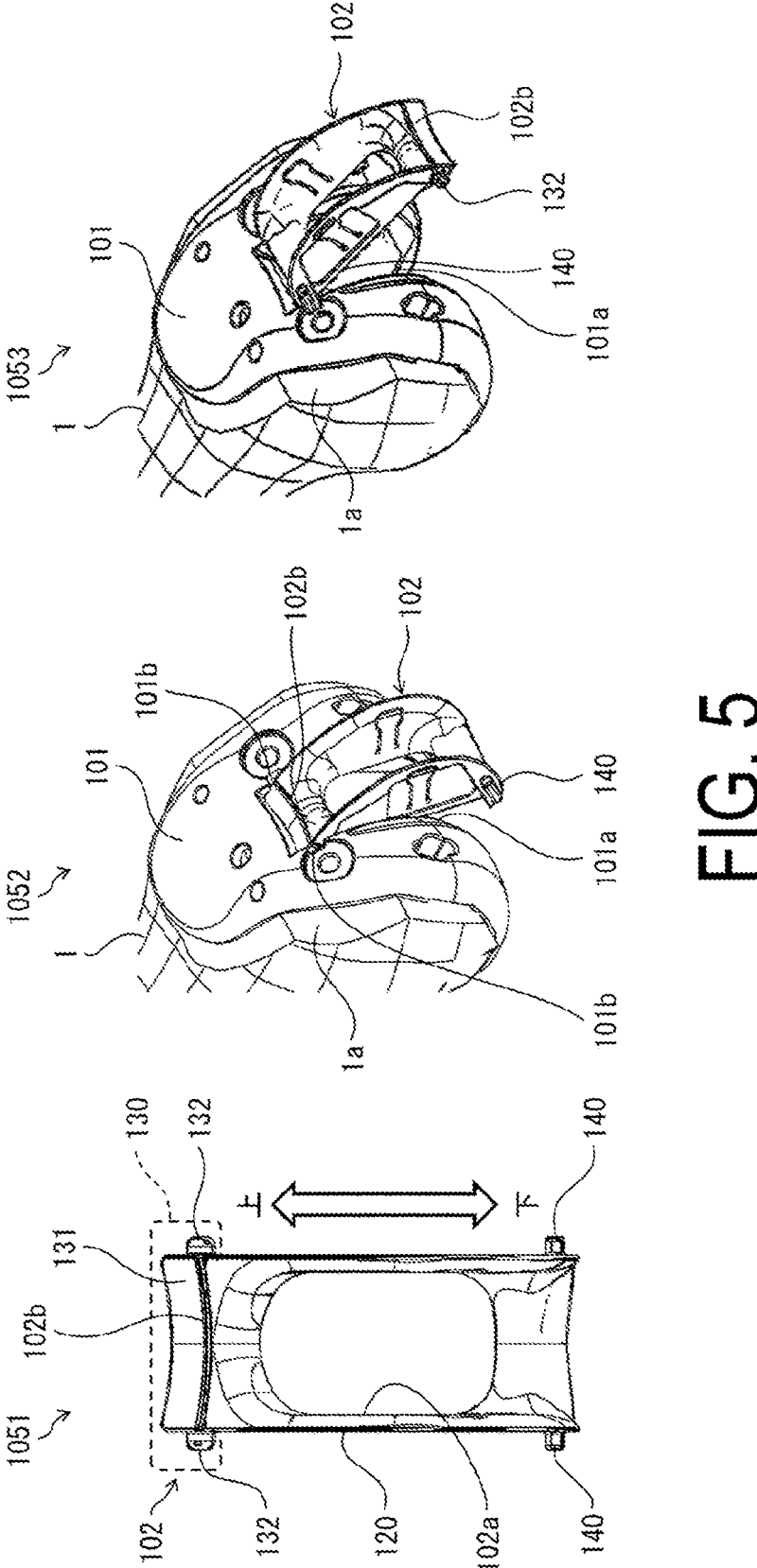
FIG. 5 is another view for explaining a method of attaching the cam module illustrated in FIG. 1 to the femoral trial.

As indicated by reference sign 1051 in FIG. 5, in the cam module 102, the slit 102*b* is formed between the first connection portion 130 having the rotation pile portion 132 and the side wall portion 120. That is, assuming that the first connection portion 130 side of the cam module 102 is an upper side and the second connection portion 140 side is a lower side, the slit 102*b* is provided on the upper side of the cam module 102. By using the slit 102*b* as a mark, the vertical direction of the cam module 102 can be easily determined.

As a result, as indicated by reference sign 1052 in FIG. 5, the rotation pile portion 132 of the cam module 102 can be easily directed toward the groove portion 101*b* side of the trial body 101. As a result, as indicated by reference sign 1053 in FIG. 5, the second connection portion 140 side of the cam module 102 can be suppressed from being directed toward the groove portion 101*b* side of the trial body 101.

In this manner, the first connection portion 130 is provided at one end portion in the longitudinal direction of the side wall portion 120 via the base portion 133 which is separate from the side wall portion 120, thus the slit 102*b* is formed at the one end portion. Accordingly, the position where the first connection portion 130 is provided in the cam module 102 can be easily grasped. Therefore, the cam module 102 can be fitted into the opening portion 101*a* of the trial body 101 of the femoral trial 100 in the correct direction.

Base Portion 133

Figure 6:
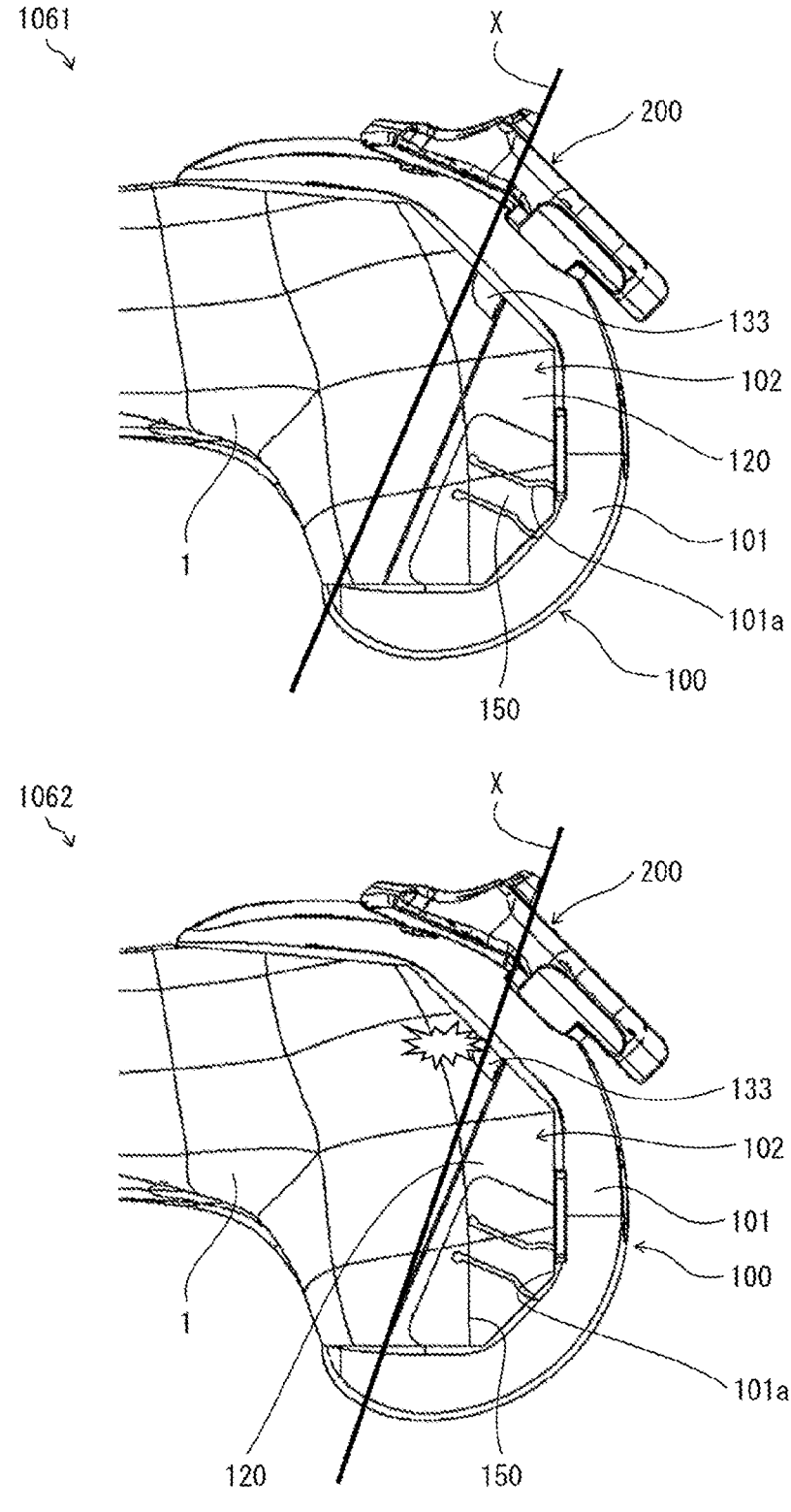
FIG. 6 is a view for explaining one function of the cam module illustrated in FIG. 4.

Reference sign 1061 in FIG. 6 indicates an osteotomy line X in a case where the intercondylar cutting guide 200, which is an osteotomy guide, functions properly upon being attached to the femoral trial 100. The osteotomy line X is a line indicating a position at which the osteotomy of the bone 1 is performed. Accordingly, if the osteotomy is correctly performed, the osteotomy line X will not extend beyond the base portion 133, assuming that the cam module 102 is attached in place on the trial body 101.

On the other hand, as indicated by reference sign 1062 in FIG. 6, if the base portion 133 comes into contact with the bone 1 upon the cam module 102 being attached to the opening portion 101*a* of the trial body 101, the osteotomy can be determined to be incorrectly performed.

That is, when the base portion 133 interferes with the bone 1 before the cam module 102 rotates to the predetermined position on the opening portion 101*a*, the osteotomy can be determined to be incorrectly performed. Accordingly, by performing the osteotomy so that the base portion 133 does not interfere with the bone 1 before the cam module 102 rotates to the predetermined position on the opening portion 102*a*, the osteotomy can be correctly performed without causing a situation in which the osteotomy is not sufficient.

Urging Member 150

Figure 7:
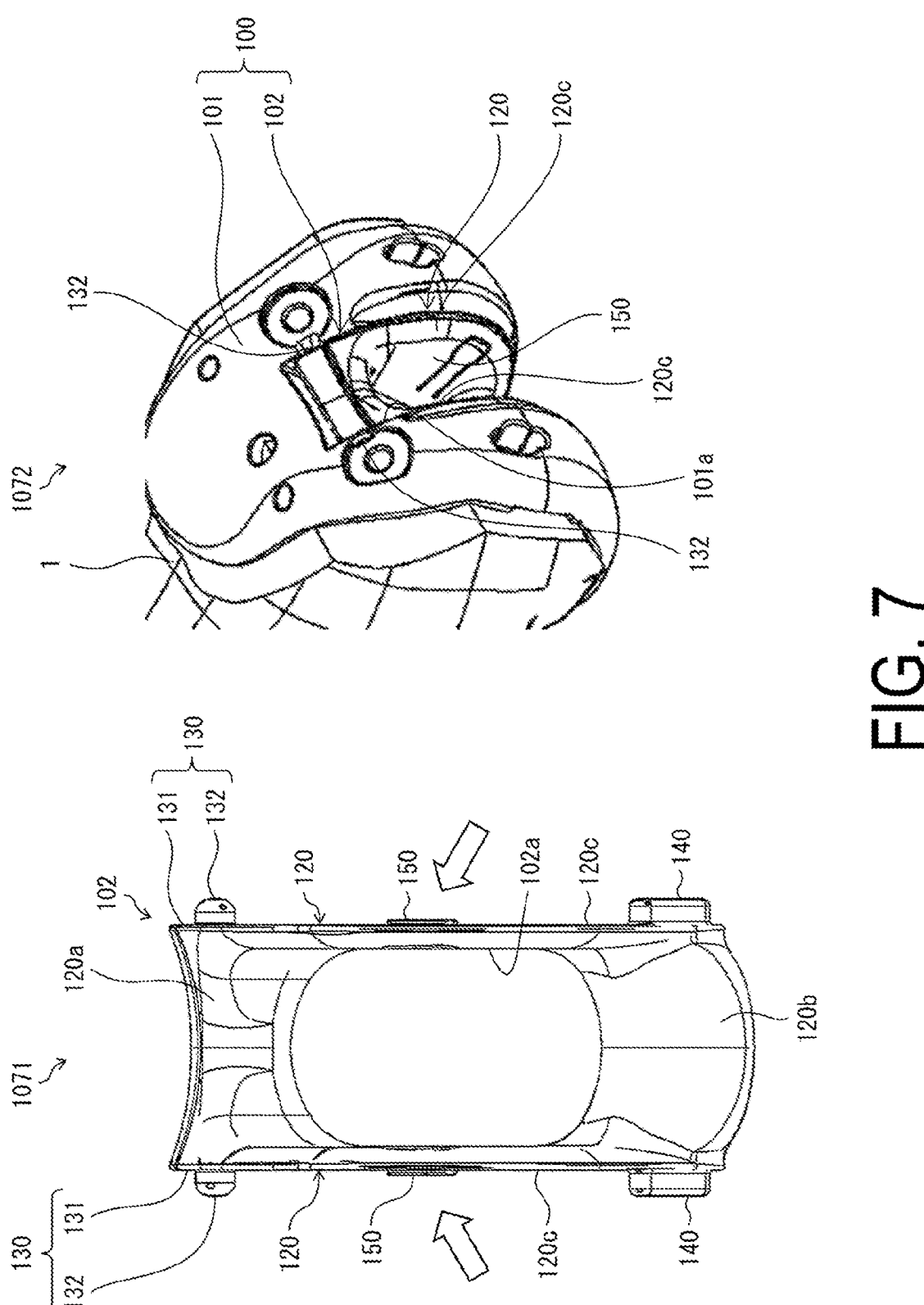
FIG. 7 is a view for explaining another function of the cam module illustrated in FIG. 4.

As indicated by reference sign 1071 in FIG. 7, in the cam module 102, the urging member 150 made of a plate spring or the like having an urging force against an external force (arrow) from the outside is provided on the side surface 120*c* at substantially the center of the side surface 120*c* of the side wall portion 120. Accordingly, as indicated by reference sign 1072 in FIG. 7, upon the cam module 102 being fitted into the opening portion 101*a* of the trial body 101, the side surface 120*c* of the side wall portion 120 is pressed against the opening portion 101*a* of the trial body 101 by the urging force of the urging member 150. Thus, the cam module 102 is held in the opening portion 101*a* of the trial body 101 by the urging force of the urging member 150, and is less likely to be detached from the opening portion 101*a*. A position at which the urging member 150 is provided on the side wall portion 120 is not particularly limited.

Second Connection Portion 140

Figure 8:
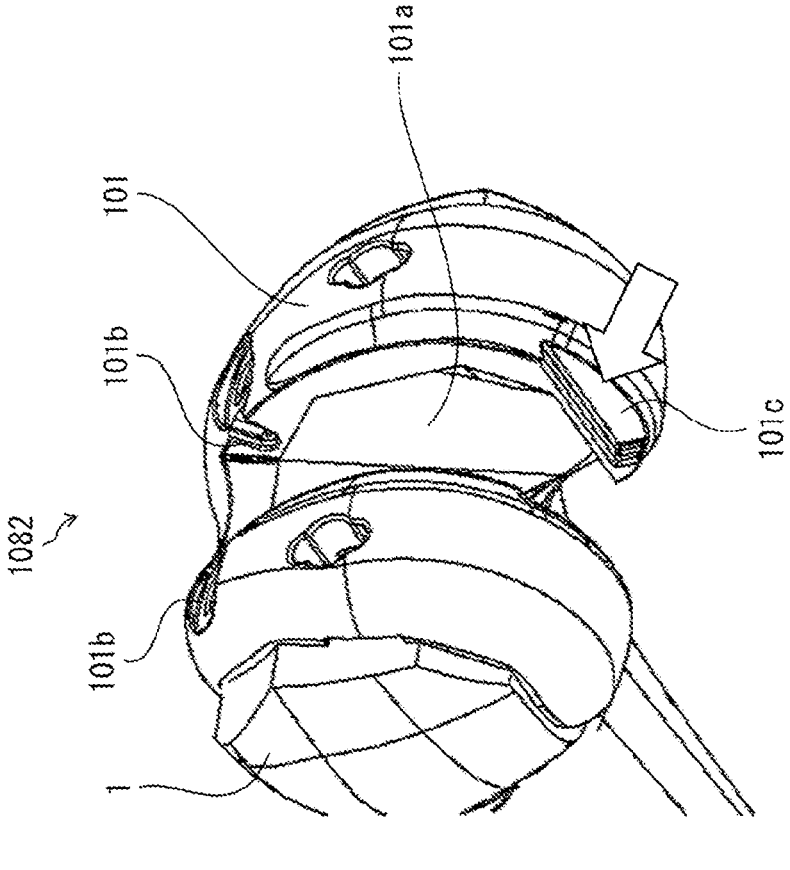
FIG. 8 is a view for explaining another function of the cam module illustrated in FIG. 4.
Figure 8:
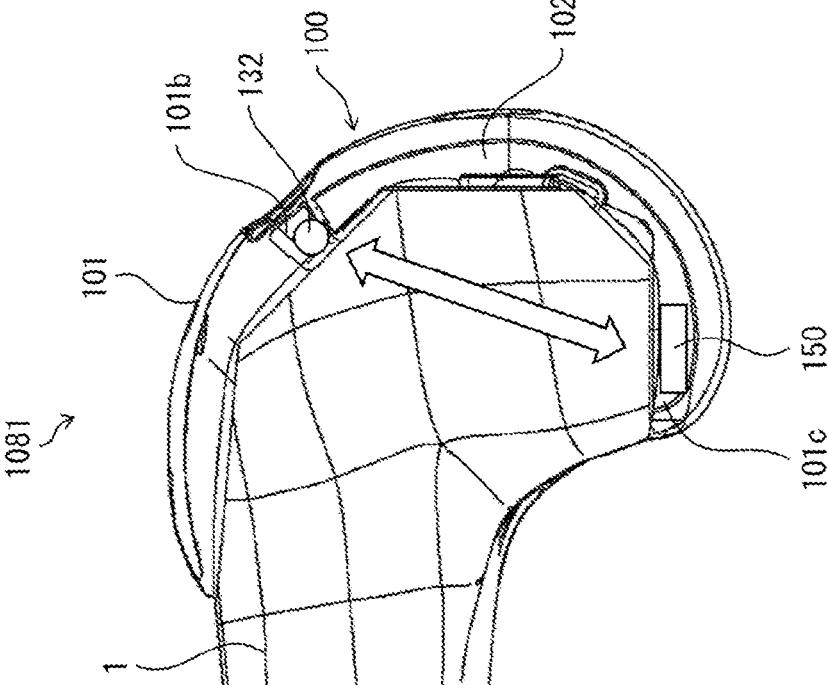

As indicated by reference sign 1082 in FIG. 8, an accommodation portion 101*c* for accommodating the second connection portion 140 of the trial body 101 is provided at the lower end of the opening portion 101*a* of the trial body 101. Accordingly, as indicated by reference sign 1081 in FIG. 8, in a state in which the cam module 102 is attached to a predetermined position on the opening portion 101*a* of the trial body 101, the rotation pile portion 132, which is one of the components of the first connection portion 130, and the second connection portion 140 are at positions separated from each other.

In this manner, the cam module 102 is connected to and supported by the trial body 101 constituting the femoral trial 100 by the first connection portion 130 disposed on the first end portion 120*a* of the side wall portion 120 in the longitudinal direction and the second connection portion 140 disposed on the second end portion 120*b* on the opposite side. That is, the cam module 102 is in a state of being supported at both end portions of the side wall portion 120 in the longitudinal direction. Therefore, the cam module 102 can be stably supported as compared with a case where the cam module 102 is supported at a position closer to the center of the side wall portion 120. As a result, the cam module 102 is less likely to be displaced and detached from the opening portion 101*a* of the trial body 101 of the femoral trial 100, and the fitting state of the cam module 102 to the opening portion 101*a* can be stably maintained. That is, the femoral trial 100 in which the cam module 102 is less loose can be provided.

The shape of the second connection portion 140 is not particularly limited as long as the second connection portion 140 can be accommodated in the 101*c* of the accommodation portion of the trial body 101. The shape of the accommodation portion 101*c* accommodating the second connection portion 140 is not particularly limited, and may be a shape that can appropriately accommodate the second connection portion 140 upon the cam module 102 being rotated to a predetermined position.

Second Embodiment

Figure 9:
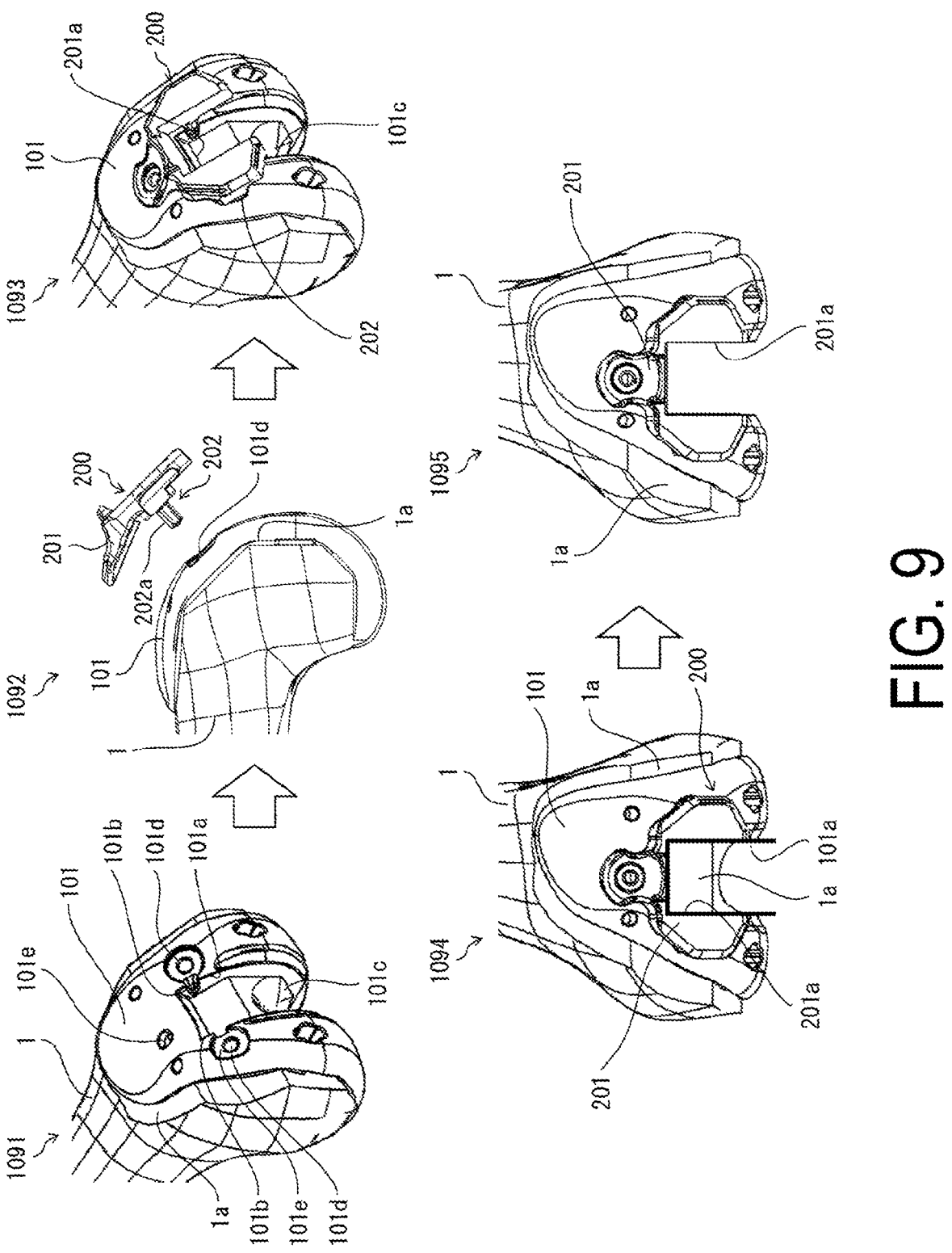
FIG. 9 is a view for explaining a procedure up to an osteotomy of an intercondylar portion using a femoral trial according to a second embodiment of the present disclosure.

Another embodiment of the present disclosure will be described below. For convenience of description, a member having the same function as that of a member described in the embodiments described above is denoted by the same reference sign, and description thereof will not be repeated.
Outline of Intercondylar Cutting Guide FIG. 9 is a view for explaining the procedure for an osteotomy using the intercondylar cutting guide 200. As illustrated in FIG. 9, the intercondylar cutting guide 200 is attached along the opening portion 101a of the trial body 101 constituting the femoral trial 100, thereby guiding the osteotomy of the knee joint 1a of the bone 1 exposed to the opening portion 101a of the trial body 101. Details of the intercondylar cutting guide 200 will be described below.

In order to attach the intercondylar cutting guide 200, as indicated by reference sign 1091 in FIG. 9, the trial body 101 has partial-hole portions 101d, 101d formed adjacent to the groove portions 101b formed on both sides of the upper portion of the opening portion 101a. In the trial body 101, a through hole 101e is formed on the upper side of the opening portion 101a. A contact plane portion 101f coming into contact with a plane portion 202b of an attachment portion 202 of the intercondylar cutting guide 200 to be described below is formed around the partial-hole portion 101d. A trial-side attachment portion for attaching the intercondylar cutting guide 200 to the trial body 101 includes the partial-hole portion 101d, the through hole 101e, and the contact plane portion 101f. Each of the plane portion 202b and the contact plane portion 101f is not intended to be a curved surface at a visible level or to have no unevenness at a visible level, and is not required to be strictly flat.

As indicated by reference sign 1092 in FIG. 9, a protrusion portion 202a of the attachment portion 202 provided in a cutting guide portion 201 of the intercondylar cutting guide 200 is inserted into the partial-hole portion 101d. By inserting the protrusion portion 202a into the partial-hole portion 101d of the cam module 102, the intercondylar cutting guide 200 is attached to a predetermined position on the trial body 101, as indicated by reference sign 1093 in FIG. 9.

Figure 10:
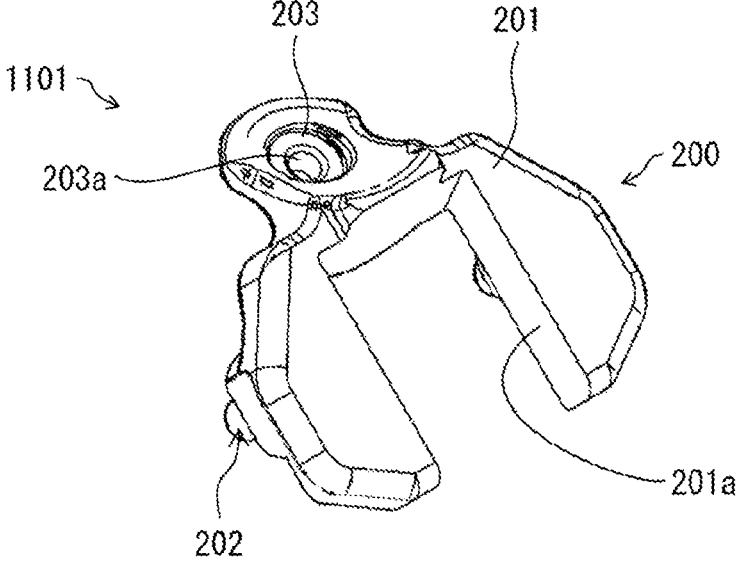
FIG. 10 is a schematic configuration diagram of an intercondylar cutting guide attached to the femoral trial illustrated in FIG. 9.
Figure 10:
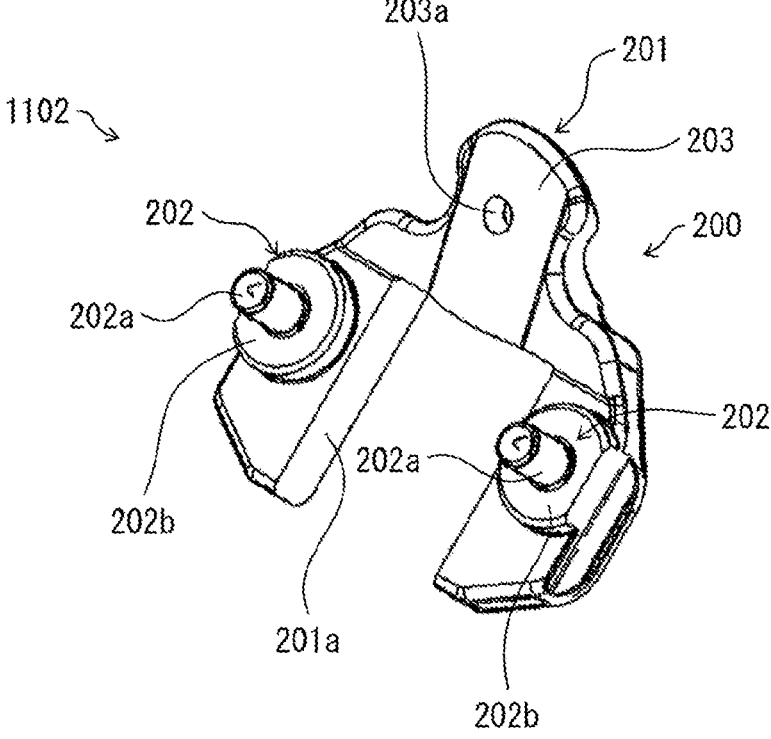

Before the osteotomy, as indicated by reference sign 1094 in FIG. 9, in a state where the intercondylar cutting guide 200 is attached to the trial body 101, the knee joint 1a of the bone 1 is exposed from the opening portion 201b of the cutting guide portion 201. By performing the osteotomy accurately along the intercondylar cutting guide 200, as indicated by reference sign 1095 in FIG. 9, the knee joint 1a of the bone 1 is resected from an opening portion 201a of the cutting guide portion 201.
Details of Intercondylar Cutting Guide As illustrated in FIG. 10, the intercondylar cutting guide 200 includes the cutting guide portion 201, the attachment portion 202, and a pin insertion portion 203. The cutting guide portion 201 has the opening portion 201a exposed in accordance with the shape of the opening portion 101a of the trial body 101 constituting the femoral trial 100. The attachment portion 202 attaches the cutting guide portion 201 to a predetermined position in the trial body 101 of the femoral trial 100. The pin insertion portion 203 is used to fix the cutting guide portion 201 to the trial body 101.

The attachment portion 202 includes the protrusion portion 202a to be inserted into the partial-hole portion 101d formed at an attachment position on the intercondylar cutting guide 200 in the trial body 101, and a plane portion 202b capable of coming into contact with the contact plane portion 101f formed around the partial-hole portion 101d. The attachment portion 202 has a magnet (not illustrated) incorporated therein, and the incorporated magnet exerts a magnetic force on the contact plane portion 101f.
Attachment of Intercondylar Cutting Guide The attachment of the intercondylar cutting guide 200 illustrated in FIG. 10 to the trial body 101 will be described based on the structural features of the intercondylar cutting guide 200.

The attachment portion 202 incorporates a magnet for exerting a magnetic force on the contact plane portion 101f of the trial body 101. In the present embodiment, the contact plane portion 101f of the trial body 101 includes a ferromagnetic material such as 400 series or 600 series stainless steel, for example, which may facilitate attachment and detachment of the cutting guide portion 201 to and from the trial body 101.

Upon the intercondylar cutting guide 200 being attached to the trial body 101, the protrusion portion 202a of the attachment portion 202 is inserted into the partial-hole portion 101d, and the plane portion 202b of the attachment portion 202 comes into surface contact with the contact plane portion 101f. Accordingly, the intercondylar cutting guide 200 can be stably attached to the trial body 101.
Pin Insertion Portion The attachment of the intercondylar cutting guide 200 to the trial body 101 can be performed sufficiently stably by using the attachment portion 202. In order to further stabilize the attachment of the intercondylar cutting guide 200 to the trial body 101, the pin insertion portion 203 provided in the cutting guide portion 201, which is denoted by reference sign 1101 in FIG. 10, is used.

The pin insertion portion 203 is disposed at a position facing the through hole 101e disposed at the attachment position on the intercondylar cutting guide 200 in the femoral trial 100, and has a hole portion 203a through which a pin 204 passing through the through hole 101e can be inserted.

Figure 11:
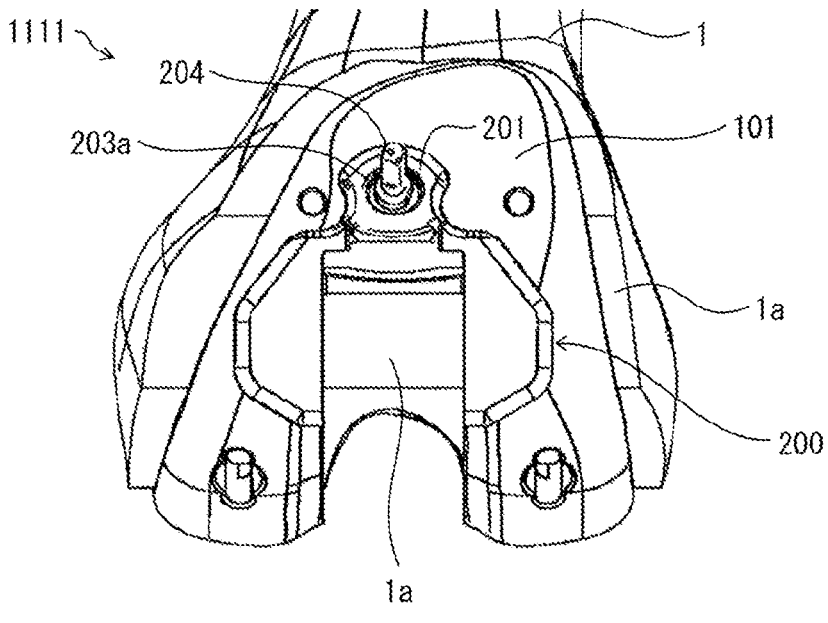
FIG. 11 is a view for explaining another function of the intercondylar cutting guide attached to the femoral trial illustrated in FIG. 9.
Figure 11:
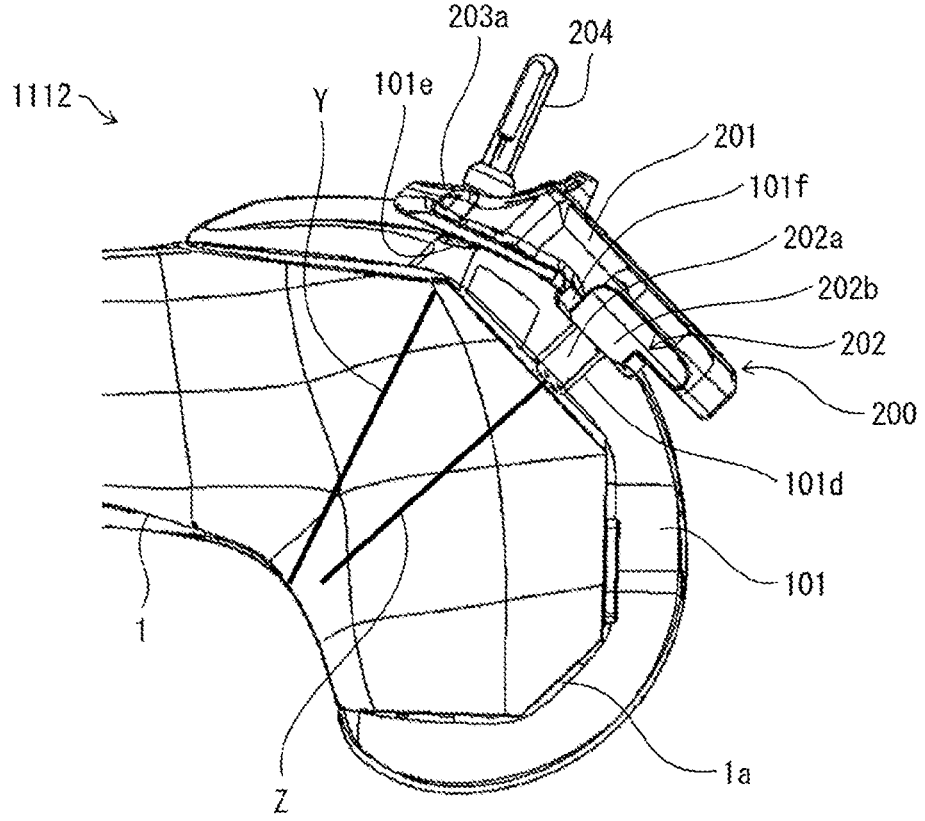

As indicated by reference sign 1111 in FIG. 11, the pin 204 is passed through the through hole 101e of the trial body 101 through the hole portion 203a of the pin insertion portion 203. At this time, the protrusion portion 202a of the attachment portion 202 of the cutting guide portion 201 is inserted into the partial-hole portion 101d of the trial body 101. Therefore, the intercondylar cutting guide 200 is fixed to the trial body 101 by the pin 204 and the protrusion portion 202a of the attachment portion 202. That is, a fixing portion for fixing the intercondylar cutting guide 200 to the trial body 101 is formed by the hole portion 203a of the pin insertion portion 203 and the protrusion portion 202a (projecting portion) of the attachment portion 202 in the intercondylar cutting guide 200.

In this manner, by driving the pin 204 into the intercondylar cutting guide 200, the intercondylar cutting guide 200 can be fixed to the trial body 101.

In addition, as indicated by reference sign 1112 in FIG. 11, the hole portion 203a and the protrusion portion 202a are disposed such that the axis Y of the pin 204 inserted into the hole portion 203a and the axis Z of the protrusion portion 202a are in different directions. This may facilitate detachment of the intercondylar cutting guide 200 from the trial body 101, thereby suppressing the intercondylar cutting guide 200 from floating due to the vibration of the bone saw. The directions of the axes Y and Z are not particularly limited as long as they are not parallel to each other.

Figure 12:
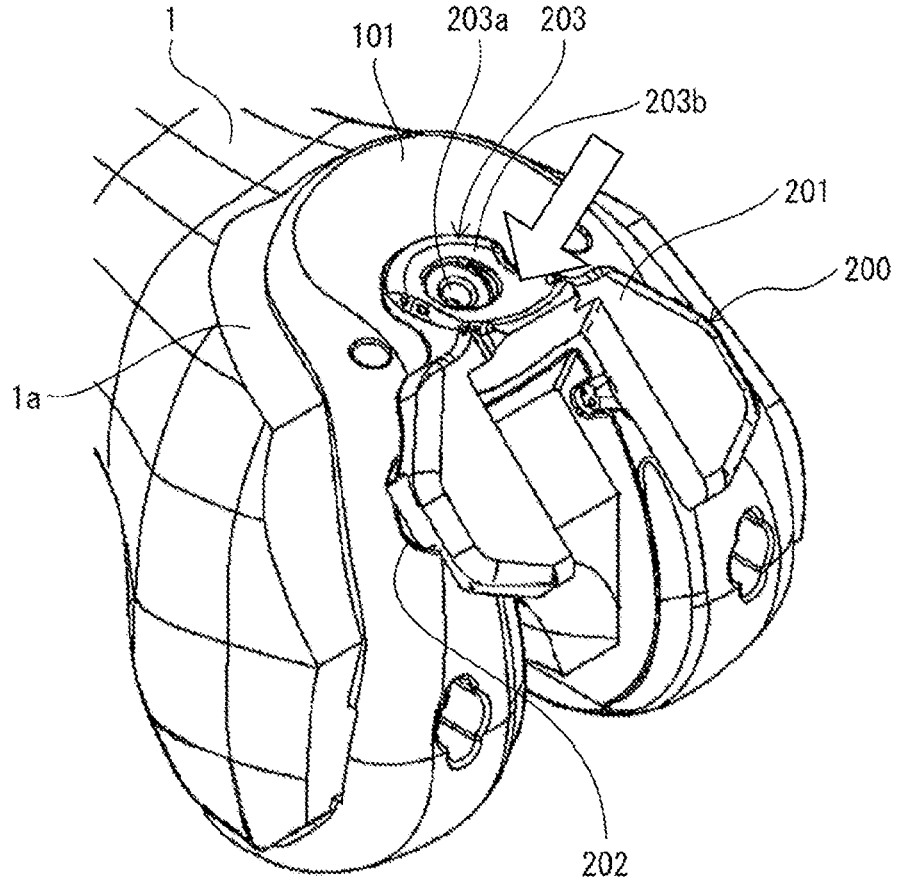
FIG. 12 is a view for explaining another function of the intercondylar cutting guide attached to the femoral trial illustrated in FIG. 9.

As illustrated in FIG. 12, the pin insertion portion 203 forms a recessed portion 203b in which the periphery of the hole portion 203a is recessed. Therefore, instead of inserting the pin 204 into the hole portion 203a of the pin insertion portion 203, the surgeon can press the recessed portion 203b with a finger so as not to float.

Third Embodiment

Another embodiment of the present disclosure will be described below. For convenience of description, a member having the same function as that of a member described in the embodiments described above is denoted by the same reference sign, and description thereof will not be repeated.

In the present embodiment, a method of detaching the femoral trial 100 attached to the bone 1 will be described.
Detachment Method (1)

First, an example in which the trial body 101 and the cam module 102 constituting the femoral trial 100 are separately detached will be described.

Figure 13:
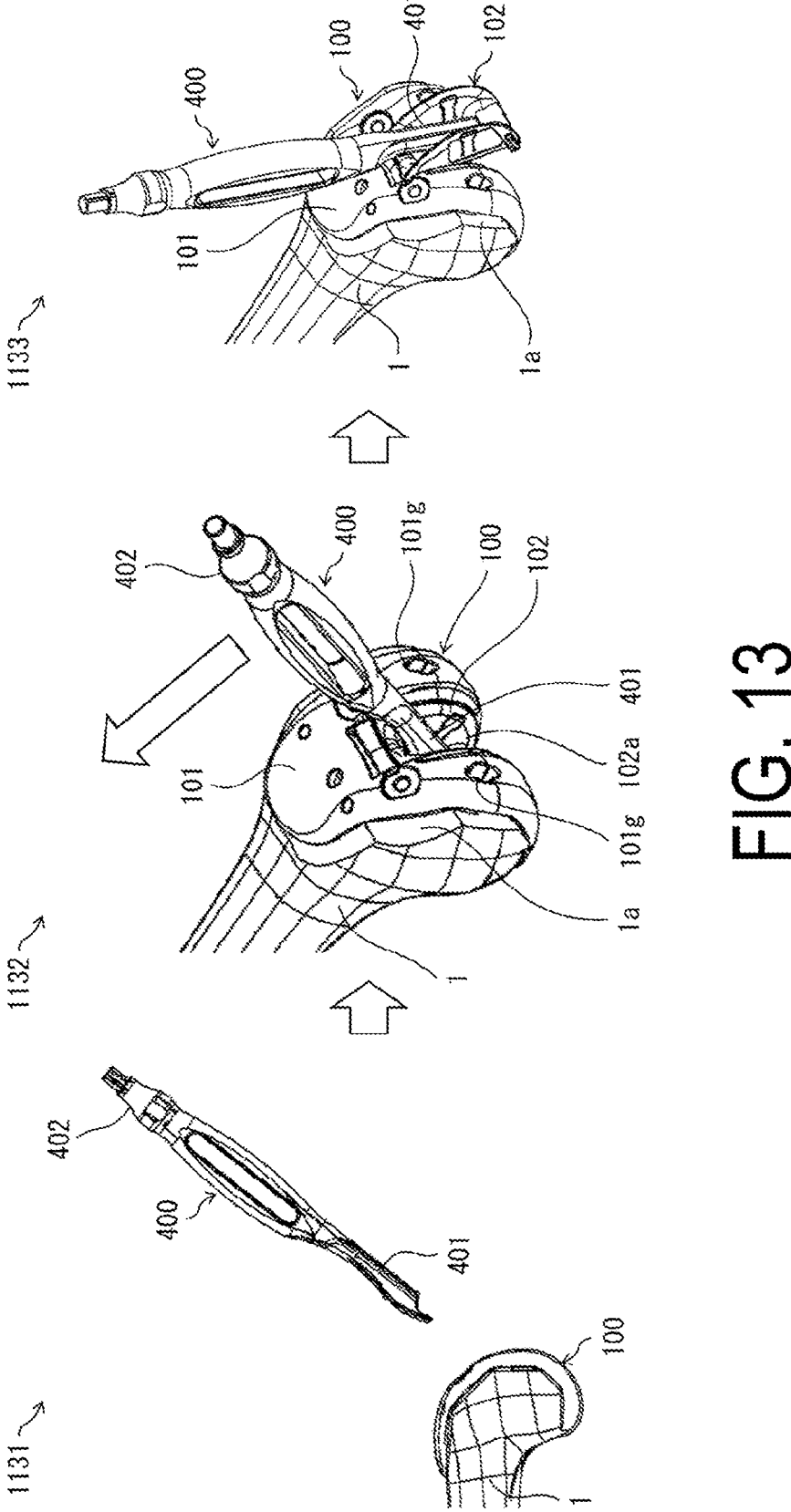
FIG. 13 is a view for explaining a method of detaching the cam module from the femoral trial.
Figure 14:
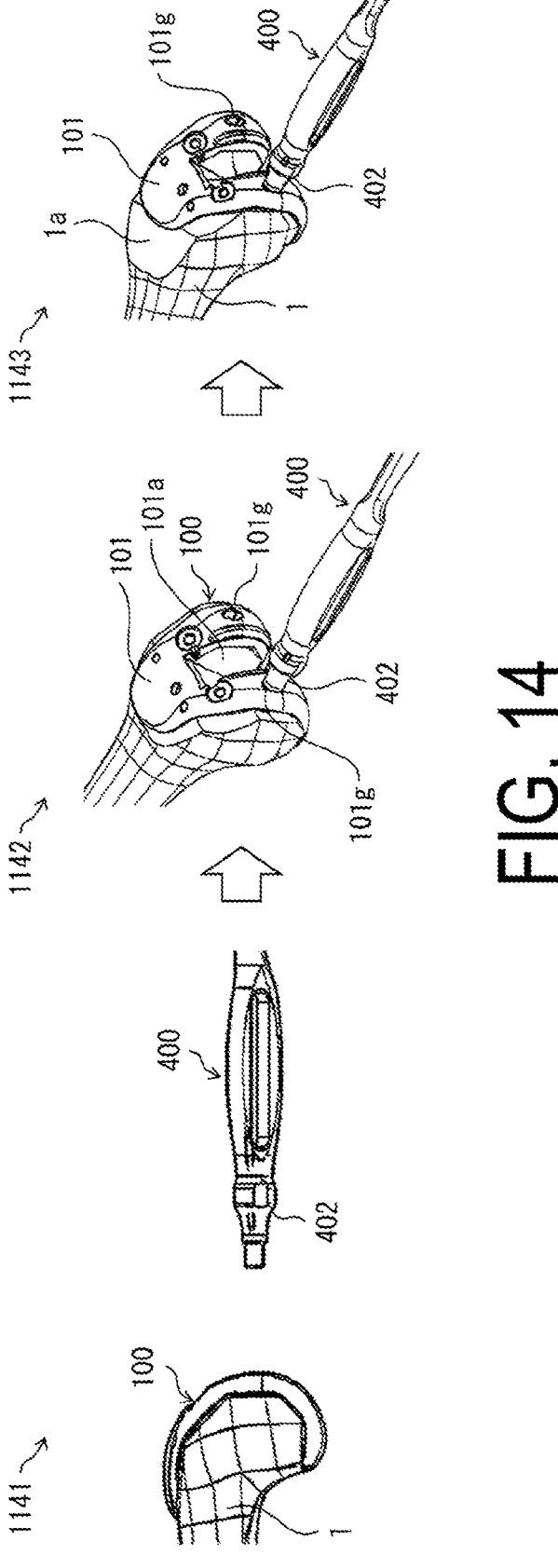
FIG. 14 is a view for explaining a method of detaching the femoral trial from a bone.

FIG. 13 is a view illustrating a procedure for detaching the cam module 102. FIG. 14 is a view illustrating a procedure for detaching the trial body 101.

The detachment of the femoral trial 100 involves the use of a slap hammer 400.

The slap hammer 400 has a first tip portion 401 provided at one end portion in the longitudinal direction and a second tip portion 402 provided at the other end portion in the longitudinal direction. The first tip portion 401 is used to detach the cam module 102, and a tip of the first tip portion 401 has a shape that can be hooked from the inside of the opening portion 102a of the cam module 102. The second tip portion 402 is used to detach the trial body 101, and the tip of the second tip portion 402 has a shape to be engaged with an engagement hole 101g of the trial body 101.

A procedure for detaching the femoral trial 100 using the slap hammer 400 having the above-described configuration will be described below. Although the detachment of the femoral trial 100 is performed by a doctor or a technician, a user who uses the slap hammer 400 will be described here.
Procedure for Detaching Cam Module 102

First, as indicated by reference sign 1131 in FIG. 13, the user inserts the first tip portion 401 of the slap hammer 400 into the opening portion 102a of the cam module 102 from the side of the femoral trial 100 opposite to the bone 1 (articular surface side).

In a state where the first tip portion 401 of the slap hammer 400 is inserted into the opening portion 102a of the cam module 102, the user confirms that the tip of the first tip portion 401 is hooked on the inner side of the lower end of the opening portion 102a of the cam module 102. Thereafter, as indicated by reference sign 1132 in FIG. 13, the slap hammer 400 is pushed in a direction (arrow direction) from the femoral trial 100 toward the bone 1.

According to the principle of leverage, as indicated by reference sign 1133 in FIG. 13, the second connection portion of the cam module 102 is disconnected in a state in which the tip of the first tip portion 401 of the slap hammer 400 is hooked on the inner side of the lower end of the opening portion 102a of the cam module 102.

Finally, the user detaches the first tip portion 401 of the slap hammer 400 from the opening portion 102a of the cam module 102 to disconnect the first connection portion 130 of the cam module 102, and detaches the cam module 102 from the trial body 101.
Procedure for Detaching Trial Body 101

As indicated by reference sign 1141 in FIG. 14, in a state in which the cam module 102 is detached, the user inserts the second tip portion 402 of the slap hammer 400 into the engagement hole 101g of the trial body 101 from the side opposite to the bone 1 with respect to the femoral trial 100 and engages the second tip portion 402 with the engagement hole 101g.

The user pushes the second tip portion 402 of the slap hammer 400 in a predetermined direction in a state of being engaged with the engagement hole 101g of the trial body 101. To be specific, as indicated by reference sign 1142 in FIG. 14, the slap hammer 400 is pushed in a direction (arrow direction) orthogonal to the insertion direction of the second tip portion 402 into the engagement hole 101g and toward the opposite side to the opening portion 101a of the trial body 101.

According to the principle of leverage, as indicated by reference sign 1143 in FIG. 14, in a state in which the tip of the second tip portion 402 of the slap hammer 400 is engaged with the engagement hole 101g of the trial body 101, the attachment portion between the trial body 101 and the bone 1 is loosened.

Finally, the user detaches the second tip portion 402 of the slap hammer 400 from the engagement hole 101g of the trial body 101 to detach the trial body 101 from the bone 1.
Detachment Method (2)

A procedure for detaching the femoral trial 100 from the bone 1 in a state where the cam module 102 is fitted to the trial body 101 will be described.

Figure 15:
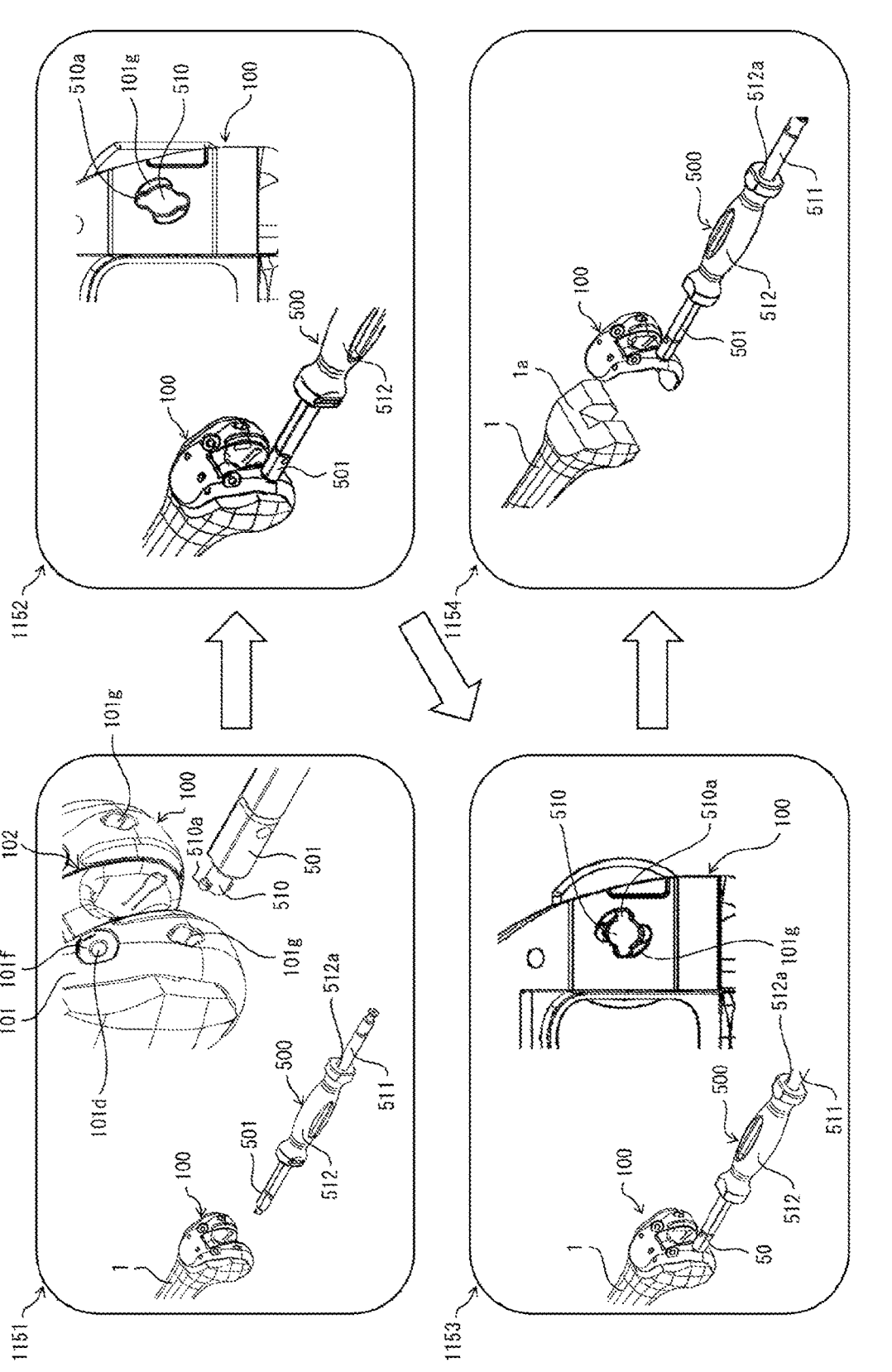
FIG. 15 is a view for explaining a method of detaching the femoral trial from the bone in a state in which the cam module is attached.

FIG. 15 is a view illustrating a procedure for detaching the femoral trial 100. The detachment of the femoral trial 100 involves the use of a slap hammer 500.

The slap hammer 500 includes a shaft 511 extending in the longitudinal direction, and a handle 512 through which the shaft 511 can be inserted and which is slidable in the longitudinal direction. An opening portion 512a of the handle 512 through which the shaft 511 is inserted has a circular shape. The shaft 511 has a first tip portion 501 provided at one end portion in the longitudinal direction. The first tip portion 501 has an engagement portion 510 to be engaged with the engagement hole 101g of the trial body 101. Two projecting portions 510a protruding outward in a direction orthogonal to the axial direction of the first tip portion 501 are formed at the tip of the engagement portion 510. Here, the engagement hole 101g of the trial body 101 is formed so that the engagement portion 510 is inserted together with the projecting portions 510a and rotated in a certain direction to engage with the inserted projecting portion 510a. That is, the engagement hole 101g of the trial body 101 is formed so that the two projecting portions 510a can be inserted, and is formed so that the projecting portions 510a are engaged with the engagement hole 101g by rotating the projecting portions 510a in a certain direction therein.

A procedure for detaching the femoral trial 100 using the slap hammer 500 having the above-described configuration will be described below. Although the detachment of the femoral trial 100 is performed by a doctor or a technician, a user who uses the slap hammer 500 will be described here.
Detachment Procedure for Femoral Trial 100

First, as indicated by reference sign 1151 in FIG. 15, the user inserts the first tip portion 501 of the first tip portion 501 of the slap hammer 500 into the engagement hole 101g of the trial body 101 from the side of the femoral trial 100 opposite to the bone 1 (articular surface side). At this time, the engagement portion 510 is inserted into the engagement hole 101g while adjusting the direction of the projecting portions 510a of the engagement portion 510. Accordingly, as indicated by reference sign 1152 in FIG. 15, as viewed from the bone 1 side of the femoral trial 100, the first tip portion 501 has the projecting portions 510a inserted along the inner shape of the engagement hole 101g and the first tip portion 501 protrudes from the engagement hole 101g.

The user rotates the slap hammer 500 about the shaft in a state in which the engagement portion 510 of the first tip portion 501 of the slap hammer 500 is inserted into the engagement hole 101g of the trial body 101. Accordingly, as indicated by reference sign 1153 in FIG. 15, as viewed from the bone 1 side of the femoral trial 100, the positions of the projecting portions 510a of the first tip portion 501 are deviated from the shape of the engagement hole 101g, and thus the projecting portions 510a are locked on the bone 1 side (back surface side) of the trial body 101.

Finally, after confirming that the convex portions 510a are locked on the bone 1 side (back surface side) of the trial body 101, the user detaches the femoral trial 100 from the bone 1 by moving the slap hammer 500 away from the bone 1, as indicated by reference sign 1154 in FIG. 15.

In this manner, by using the slap hammer 500, the femoral trial 100 can be detached from the bone 1 in a state in which the cam module 102 is attached to the trial body 101.

In the present disclosure, the invention has been described above based on the various drawings and examples. However, the invention according to the present disclosure is not limited to each embodiment described above. That is, the embodiments of the invention according to the present disclosure can be modified in various ways within the scope illustrated in the present disclosure, and embodiments obtained by appropriately combining the technical means disclosed in different embodiments are also included in the technical scope of the invention according to the present disclosure. In other words, note that a person skilled in the art can easily make various variations or modifications based on the present disclosure. Note that these variations or modifications are included within the scope of the present disclosure. For example, a configuration including the femoral trial 100, the cam module 102, and the intercondylar cutting guide 200 described above may be considered as one system. In this system, the cam module 102 and the intercondylar cutting guide 200 cannot be attached to the femoral trial 100 at the same time, but only one of them can be attached. The system may also include the slap hammers 400, 500 described above for use in detaching the femoral trial 100.

REFERENCE SIGNS

1 Bone
1a Knee joint
2 Artificial knee joint
100 Femoral trial
101 Trial body
101a, 102a, 201a, 201b Opening portion
101b Groove portion
101c Accommodation portion
101d, 101d, 101d Partial-hole portion
101e Through hole
101f Contact plane portion
101g Engagement hole
102 Cam module

102b Slit
120 Side wall portion
120a First end portion
120b Second end portion
120C Side surface
130 First connection portion
131 Body portion
132 Rotation pile portion
133 Base portion
140 Second connection portion
150 Urging member
200 Intercondylar cutting guide
201 cutting guide portion
202 Attachment portion
202a Protrusion portion
202b Plane portion
203 Pin insertion portion
203a Hole portion
203b Recessed portion
204 Pin
400, 500 Slap hammer
401, 501 First tip portion
402 Second tip portion
510 Engagement portion
510a Projecting portion

The invention claimed is:

1. A cam module comprising:

a pair of side wall portions, each side wall portion comprising a first end portion and a second end portion different from the first end portion in a longitudinal direction;

a first connection portion disposed at the first end portion of the pair of side wall portions and connectable to a femoral trial; and a second connection portion disposed at the second end portion of the pair of side wall portions and connectable to the femoral trial, the cam module configured to fit into an opening portion of the femoral trial, wherein the cam module further comprises a rotation pile portion that is configured to be rotatably supported at a predetermined location on the opening portion, wherein upon the cam module being rotated to a predetermined position in the opening portion, the second connection portion is configured to come into contact with the femoral trial, the first connection portion comprises a first connection portion body portion, the rotation pile portion, and a base portion, the base portion being connected to a bone side of the first end portion, and the base portion has a shape such that the base portion protrudes from the body portion toward the bone side, and has a length such that the base portion is configured to not come into contact with a bone upon the cam module being rotated to the predetermined position on the opening portion when an osteotomy, which is performed with use of an intercondylar cutting guide that includes a cutting guide portion exposed in accordance with a shape of the opening portion of the femoral trial, has been performed, and the base portion is configured to come into contact with the bone upon the cam module being rotated to the predetermined position on the opening portion the osteotomy has not been performed.

2. The cam module according to claim 1, further comprising an urging member at each side wall portion of the pair of side wall portions, the urging member causes an urging force toward the femoral trial and configured to come into contact with the femoral trial upon the cam module being fitted to a predetermined position in the opening portion.

3. A system comprising:
the cam module according to claim 1;
a femoral trial; and
an intercondylar cutting guide, wherein
the femoral trial comprises:
    an opening portion for fitting the cam module comprising a pair of side wall portions, each side wall portion comprising a first end portion and a second end portion different from the first end portion in a longitudinal direction, a first connection portion disposed at the first end portion of the pair of side wall portions, and a second connection portion disposed at the second end portion of the pair of side wall portions, wherein
    the opening portion further comprises:
    a support portion supporting the first connection portion disposed in the cam module on a front side; and
    a contact portion on a rear side of which the second connection portion disposed in the cam module comes into contact, and
the intercondylar cutting guide comprises:
    a cutting guide portion that is exposed in accordance with a shape of an opening portion of a femoral trial; and
    an attachment portion configured to attach the cutting guide portion to a predetermined position on the femoral trial by a magnetic force, wherein the intercondylar cutting guide configured to guide an osteotomy through the opening portion.

4. The system of claim 3, wherein
either one of the cam module or the intercondylar cutting guide is attachable to the femoral trial at the same time.

5. The system of claim 3, further comprising:
a slap hammer comprising a first tip portion and a second tip portion, the first tip portion being engageable with the cam module, and the second tip portion being engageable with the femoral trial.

6. The system according to claim 3, further comprising:
a slap hammer comprising a first tip portion provided at one end portion in a longitudinal direction, the first tip portion comprising an engagement portion engageable with an engagement hole of the femoral trial, and two projecting portions protruding outward perpendicular to an axis in the longitudinal direction at a tip of the engagement portion, and the first tip portion being engageable with the engagement hole by inserting the engagement portion into the engagement hole together with the projecting portions and rotating the engagement portion about the axis in the longitudinal direction.

7. The system according to claim 6, wherein
the slap hammer comprises
    a shaft extending along the longitudinal direction; and
    a handle through which the shaft can be inserted, and slidable in the longitudinal direction, wherein
an opening portion of the handle through which the shaft is inserted has a circular shape.

* * * * *